(12) United States Patent
Klinder et al.

(10) Patent No.: US 10,251,594 B2
(45) Date of Patent: Apr. 9, 2019

(54) VERTEBRAL FEATURE IDENTIFICATION

(71) Applicant: KONINKLIJKE PHILIPS N.V., Eindhoven (NL)

(72) Inventors: Tobias Klinder, Uelzen (DE); Eberhard Sebastian Hansis, Hamburg (DE); Michael Grass, Buchholz in der Nordheide (DE); Dirk Schaefer, Hamburg (DE); Hanno Heyke Homann, Hannover (DE); Christian Haase, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/543,466

(22) PCT Filed: Jan. 7, 2016

(86) PCT No.: PCT/EP2016/050153
§ 371 (c)(1),
(2) Date: Jul. 13, 2017

(87) PCT Pub. No.: WO2016/113165
PCT Pub. Date: Jul. 21, 2016

(65) Prior Publication Data
US 2017/0367645 A1      Dec. 28, 2017

(30) Foreign Application Priority Data

Jan. 16, 2015  (EP) ..................................... 15151457

(51) Int. Cl.
*A61B 5/00*       (2006.01)
*A61B 6/00*       (2006.01)
(Continued)

(52) U.S. Cl.
CPC ............ *A61B 5/4566* (2013.01); *A61B 6/466* (2013.01); *A61B 6/505* (2013.01); *A61B 6/5217* (2013.01);
(Continued)

(58) Field of Classification Search
CPC ......... A61B 5/4566; A61B 6/487; A61B 6/04; A61B 6/032; A61B 5/055; A61B 6/466;
(Continued)

(56) References Cited

U.S. PATENT DOCUMENTS 8,509,502 B2    8/2013 Porat
2009/0022382 A1*  1/2009 Feilkas ..................... G06T 7/20
                                                              382/131
(Continued)

FOREIGN PATENT DOCUMENTS

EP    2756804 A1    7/2014
JP    2011131040 A  7/2011

OTHER PUBLICATIONS

Klinder, Tobias et al "Automated model-based vertebra detection, identification, and segmentation in CT images", Medical Image Analysis, vol. 13, 2009, pp. 471-482.
(Continued)

*Primary Examiner* — Amandeep Saini

(57) ABSTRACT

Minimally-invasive spinal inventions are often performed using fluoroscopic imaging methods, which can give a real-time impression of the location of a surgical instrument, at the expense of a small field of view. When operating on a spinal column, a small field of view can be a problem, because a medical professional is left with no reference vertebra in the fluoroscopy image, from which to identify a vertebra, which is the subject of the intervention. Identifying contiguous vertebrae is difficult because such contiguous vertebrae are similar in shape. However, characteristic fea-
(Continued)

tures, which differentiate one vertebra from other vertebra, and which are visible in the fluoroscopic view, may be used to provide a reference.

12 Claims, 6 Drawing Sheets

(51) Int. Cl.
    *G06K 9/00*     (2006.01)
    *G06T 7/00*     (2017.01)
    *G06T 19/00*     (2011.01)
    *A61B 6/03*     (2006.01)
    *A61B 6/04*     (2006.01)
    *A61B 5/055*     (2006.01)

(52) U.S. Cl.
    CPC ........ *G06K 9/00214* (2013.01); *G06T 7/0014* (2013.01); *G06T 19/00* (2013.01); *G06T 19/006* (2013.01); *A61B 5/055* (2013.01); *A61B 6/032* (2013.01); *A61B 6/04* (2013.01); *A61B 6/487* (2013.01); *A61B 6/54* (2013.01); *A61B 2576/02* (2013.01); *G06K 2209/055* (2013.01); *G06T 2207/10072* (2013.01); *G06T 2207/30012* (2013.01); *G06T 2210/41* (2013.01)

(58) Field of Classification Search
    CPC ... A61B 6/505; A61B 6/5217; A61B 2576/02; A61B 6/54; G06T 19/006; G06T 7/0014; G06T 2207/10072; G06T 2207/30012; H05K 999/99; G06K 2209/055; G06K 9/00214
    USPC ....................................................... 382/132
    See application file for complete search history.

(56) References Cited

U.S. PATENT DOCUMENTS

2009/0091567 A1     4/2009   Fu
2011/0058720 A1     3/2011   Lu

OTHER PUBLICATIONS

Otake, Y. et al "Automatic localization of vertebral levels in x-ray fluoroscopy using 3D-2D registration: a tool to reduce wrong-site surgery", Physics in Medicine and Biology, vol. 57, 2012, pp. 5485-5508.

* cited by examiner

VERTEBRAL FEATURE IDENTIFICATION

CROSS-REFERENCE TO PRIOR APPLICATIONS

This application is the U.S. National Phase application under 35 U.S.C. § 371 of International Application No. PCT/EP2016/050153, filed on Jan. 7, 2016, which claims the benefit of European Patent Application No. 15151457.7, filed on Jan. 16, 2015. These applications are hereby incorporated by reference herein.

FIELD OF THE INVENTION

The present invention relates to a device for 3D characteristic vertebral feature identification, a medical imaging system, a method for 3D characteristic vertebral feature identification using 3D volume data, a computer program element, and a computer-readable medium.

BACKGROUND OF THE INVENTION

When performing a minimally invasive spinal intervention, a popular imaging modality is intra-operative fluoroscopy. The field of view of a fluoroscopy imager is quite small. Therefore, such an imager can simultaneously display only a few spinal vertebrae of a long spinal column, and identifying contiguous vertebrae is difficult, because such contiguous vertebrae are similar in shape. Displaying the entire spinal column is not feasible. In addition, the 2D fluoroscopy only shows 2D projections, and it is difficult to assess 3D differences from such projections. Therefore, a burden is placed upon a medical professional performing a minimally invasive spinal intervention, because they must ensure that the correct vertebral level is being treated.

EP 2 756 804 describes a system for identifying a part of a spine. Such systems can be further improved. U.S. Pat. No. 8,509,502 describes a system configured to identify a plurality of vertebrae and label each vertebra based on a 3D spinal model data and an analysis of 3D vertebral shape difference.

SUMMARY OF THE INVENTION

It would be advantageous to have an improved technique for providing 3D characteristic vertebral feature identification.

Towards this end, a first aspect of the invention provides a device for 3D characteristic vertebral feature identification, comprising an input unit, a processing unit, and an output unit.

The input unit is configured to provide processed 3D volume information representing a portion of a spinal column, wherein the processed 3D volume information is computed from a plurality of images obtained through the spinal column, and is acquired along a plurality of acquisition directions.

The processing unit is configured to generate 3D spinal model data derived from the processed 3D volume information, to select first vertebra information and second vertebra information in the 3D spinal model data, and to compute 3D characteristic vertebral feature information of the first vertebra by computing a 3D vertebral shape difference between the first vertebra information and the second vertebra information in the spinal model data.

The output unit is configured to output the 3D characteristic vertebral feature information. In the following specification, the term "outputting" means that the information in question is made available internally to the system for e.g. subsequent processing, and/or externally to a user e.g. via a display.

According to a second aspect of the invention, a method for 3D characteristic vertebral feature identification using processed 3D volume information is provided. The method comprises the following steps:

a) providing processed 3D volume information representing a portion of a spinal column, wherein the 3D volume data is computed from a plurality of images obtained through the spinal column, and is acquired along a plurality of acquisition directions;

b) generating 3D spinal model data derived from the processed 3D volume information;

c) selecting first vertebra information and second vertebra information in the 3D spinal model data;

d) computing 3D characteristic vertebral feature information of the first vertebra by computing a 3D vertebral shape difference between the first vertebra information and the second vertebra information in the spinal model data; and e) outputting the 3D characteristic vertebral feature information.

According to a third aspect of the invention, there is provided a medical imaging system, comprising a medical imaging acquisition arrangement, and an image processing arrangement.

The image processing arrangement is provided as a device as previously described.

According to a fourth aspect of the invention, there is provided a computer program element for controlling a device for displaying medical images acquired from a target as previously described, which, when being executed by a processing unit, is adapted to perform the method steps previously described.

According to a fifth aspect of the invention, a computer-readable medium having stored the computer program previously described is provided.

The computation of 3D characteristic vertebral feature information of at least a first vertebra enables pre-interventional data, such as CT data, to be used for the automatic determination of patient-specific characteristic features of vertebrae, facilitating automatic vertebral level determination when only a portion of a spinal column is visible. The automatic determination of such patient-specific characteristic features allows the identification of specific vertebral levels, even when a full spinal column is not visible in a fluoroscopy image.

The automatic determination of three-dimensional patient-specific characteristic features from pre-interventional data additionally permits the identification of an improved viewing angle for the identification of a certain vertebral level during an X-ray fluoroscopy operation. Therefore, an improved viewing direction can also be provided. The use of the improved viewing direction as a given projection view of 2D medical imaging equipment, such as X-ray fluoroscopy equipment, enables a viewer, such as a medical professional, to perceive as many characteristic vertebral features as possible. The fact that such medical imaging equipment is positioned in an optimal view direction allows for more reliable vertebral feature identification, because more patient-specific vertebral features are visible to a medical professional in the 2D view.

In the following specification, the term "processed 3D volume information" means 3D image data defining the internal arrangement of an imaged volume in the form of voxels, for example. The processed 3D volume data could originate from, for example, a CT scanner, an MRI scanner, or a C-arm imaging system. Reconstruction algorithms, which provide processed 3D volume information from a plurality of images obtained through a patient, and acquired along a plurality of acquisition directions, are known to the person skilled in the art.

In the following specification, the term "3D spinal model data" means data that has been post-processed from the processed 3D volume data, to provide outline, or volume information of a spinal column, or a portion of a spinal column, in the processed 3D volume data.

In the following specification, the term "vertebra information" means 3D spinal model data defining a specific vertebra of the spine, contained in the processed 3D volume information. Such vertebra information may be selected automatically from the 3D spinal model data, by image recognition algorithms. Alternatively, the vertebra information may be highlighted manually by a user using a workstation and graphical user interface.

In the following specification, the term "3D vertebral shape difference" means that an element of the 3D spinal model data has a voxel arrangement, which is notably different to that of another neighbouring vertebra of the patient, in the context of the rest of the 3D spinal model data. Typically, when comparing two vertebrae, the shape difference will be seen when one vertebra has an extra protrusion, caused by a spondylophyte, a fracture, or a surgical screw or an implant.

In other words, during a minimally invasive spinal intervention, it is important to identify with confidence at least one spinal vertebra in the fluoroscopy field of view. This does not, necessarily, need to be the vertebra being treated, because provided one vertebral level is identified in the field of view of the fluoroscopy equipment, the others can be identified implicitly by counting up or down. Pre-interventional data from a CT or MRI scanner is used to identify patient-specific features of at least one spinal vertebra. These features are accepted as characteristic features of the vertebra. The characteristic features allow the identification of unique vertebral segments. Patient-specific vertebral features such as spondylophytes, fractures, missing bone pieces or surgical screws and implants are three-dimensional, and therefore are best characterized using a three-dimensional shape difference. An optimal viewing direction can be computed for at least one vertebra identified as having a characteristic feature or more vertebrae having each a identified characteristic feature. The computation can be performed off line, before or during the intervention. During the intervention, the computed optimal viewing direction that may be selected among the other ones may depend on a target vertebral level information.

These and other aspects of the invention will become apparent from, and are elucidated, with reference to the embodiments described hereinafter.

BRIEF DESCRIPTION OF THE DRAWINGS

Exemplary embodiments of the invention will be described with reference to the following drawings.

DETAILED DESCRIPTION OF EMBODIMENTS

When performing minimally invasive spinal interventions, it can be difficult to identify the correct vertebral level of a spinal column. Usually, the imaging modality is intraoperative fluoroscopy, and this modality has a restricted field of view. Identifying neighbouring (contiguous) vertebrae is difficult, because such contiguous vertebrae are very similar in shape to each other. Displaying the entire spinal column is not feasible. In addition, the 2D fluoroscopy only shows 2D projections, and it is difficult to assess 3D differences from such projections. Therefore, only a few vertebrae of the spinal column are visible at one time. Identification of a specific vertebral level can be misleading if a medical professional performing the spinal intervention miscalculates the number of vertebral levels. Such a miscalculation could originate from confusion, over which vertebral level appears at the boundary of the field of view of the fluoroscopy imager's field of view. Vertebral levels are labelled sequentially, as is known in the art, as $T_1$, $T_2$, $T_3$, et cetera.

Figure 2:
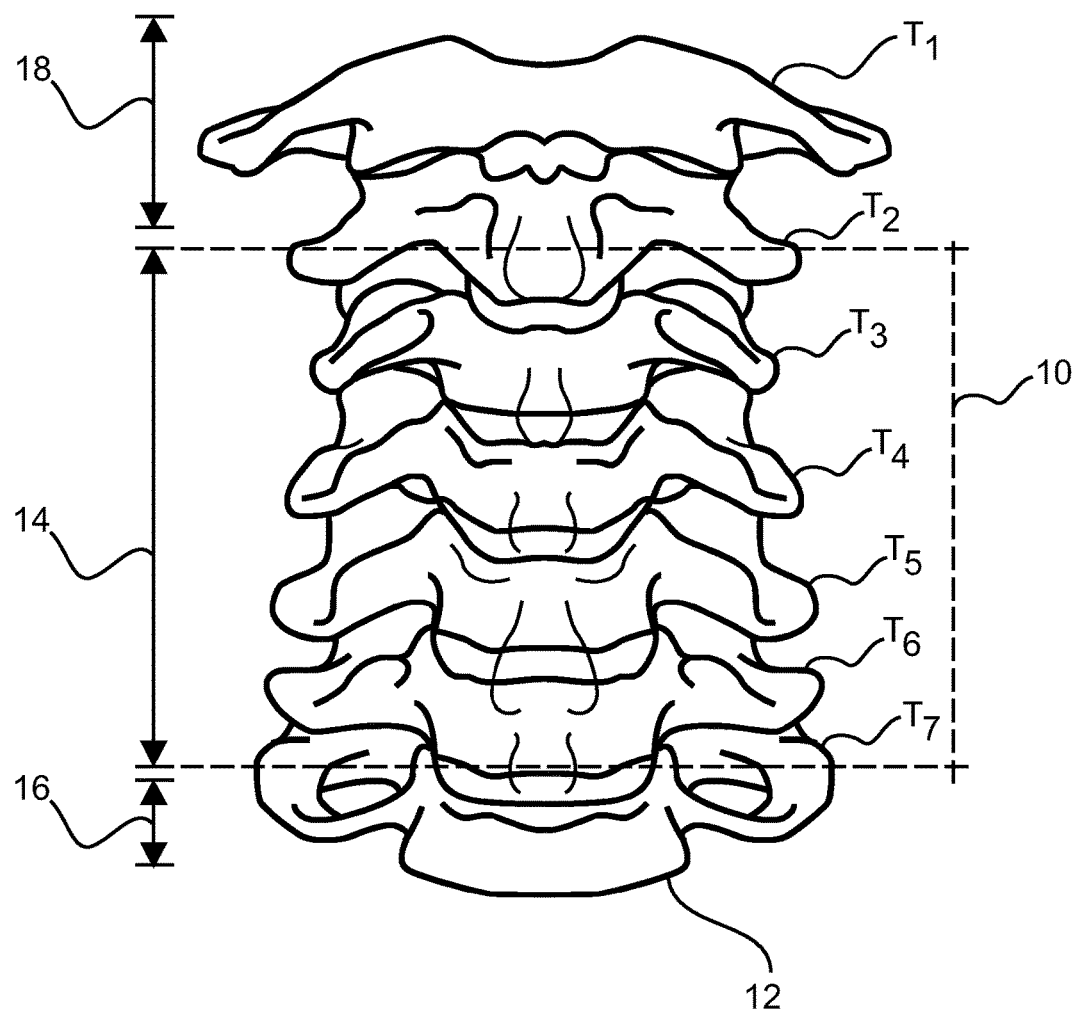
FIG. 2 shows a segment of spinal column.

FIG. 2 illustrates such a situation. A spinal column 12 comprising seven vertebrae is shown. The vertebrae are labelled $T_1$ to $T_7$. An effective field of view 10 of a fluoroscopy imager is shown by a dotted boundary. There is a region 14 of vertebrae within the field of view, such as vertebrae $T_2$, $T_3$, $T_4$, $T_5$. Vertebrae $T_1$ and $T_2$ fall in an upper excluded area 16 of the fluoroscopy imager's field of view. $T_7$ is excluded from a bottom of the fluoroscopy imager's field of view 18. If a minimally-invasive surgical intervention was performed on vertebra $T_4$, and the medical professional had no prior knowledge of the positioning of the fluoroscopy field of view 10 with respect to the rest of the spinal column, it would be easy for the medical professional to perform, incorrectly, the intervention in vertebra $T_3$, or vertebra $T_5$. Thus, for example, it could be difficult to assess whether, given sequence $T_4$-$T_5$-$T_6$, one is looking at sequence $T_3$-$T_4$-$T_5$, $T_4$-$T_5$-$T_6$, or $T_5$-$T_6$-$T_7$.

Figure 1:
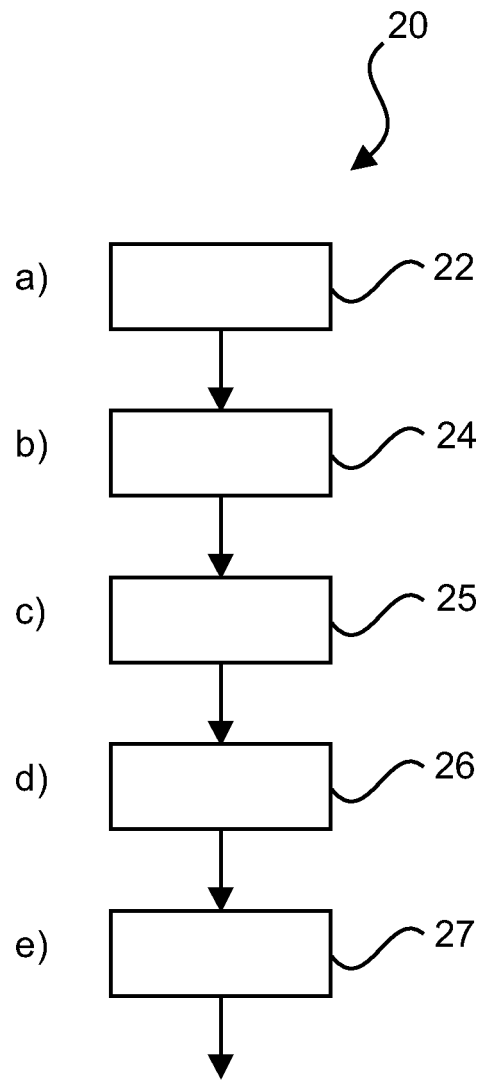
FIG. 1 shows an example of a method according to an aspect of the invention.

FIG. 1 illustrates that, according to an aspect of the invention, a method 20 for 3D characteristic vertebral feature identification using processed 3D volume information is provided, comprising the following steps:

a) providing 22 processed 3D volume information representing a portion of a spinal column, wherein the processed 3D volume information is computed from a plurality of images obtained through the spinal column, and is acquired along a plurality of acquisition directions;

b) generating 24 3D spinal model data derived from the processed 3D volume information;

c) selecting 25 first vertebra information and second vertebra information in the 3D spinal model data;

d) computing 26 3D characteristic vertebral feature information of the first vertebra by computing a 3D vertebral shape difference between the first vertebra information and the second vertebra information in the 3D spinal model data; and e) outputting 27 the 3D characteristic vertebral feature information.

Accordingly, the automatic determination of 3D patient-specific characteristic features for vertebral level identification is possible, using pre-interventional volume data obtained from a CT scanner, or an MRI scanner. This additionally allows the identification of an optimal viewing angle for vertebral level identification in medical imaging, because the pre-interventional volume data may be used to calculate the occlusion of the derived 3D characteristic vertebral feature information by a spine, for example, at various forward-projection angles.

Figure 3:
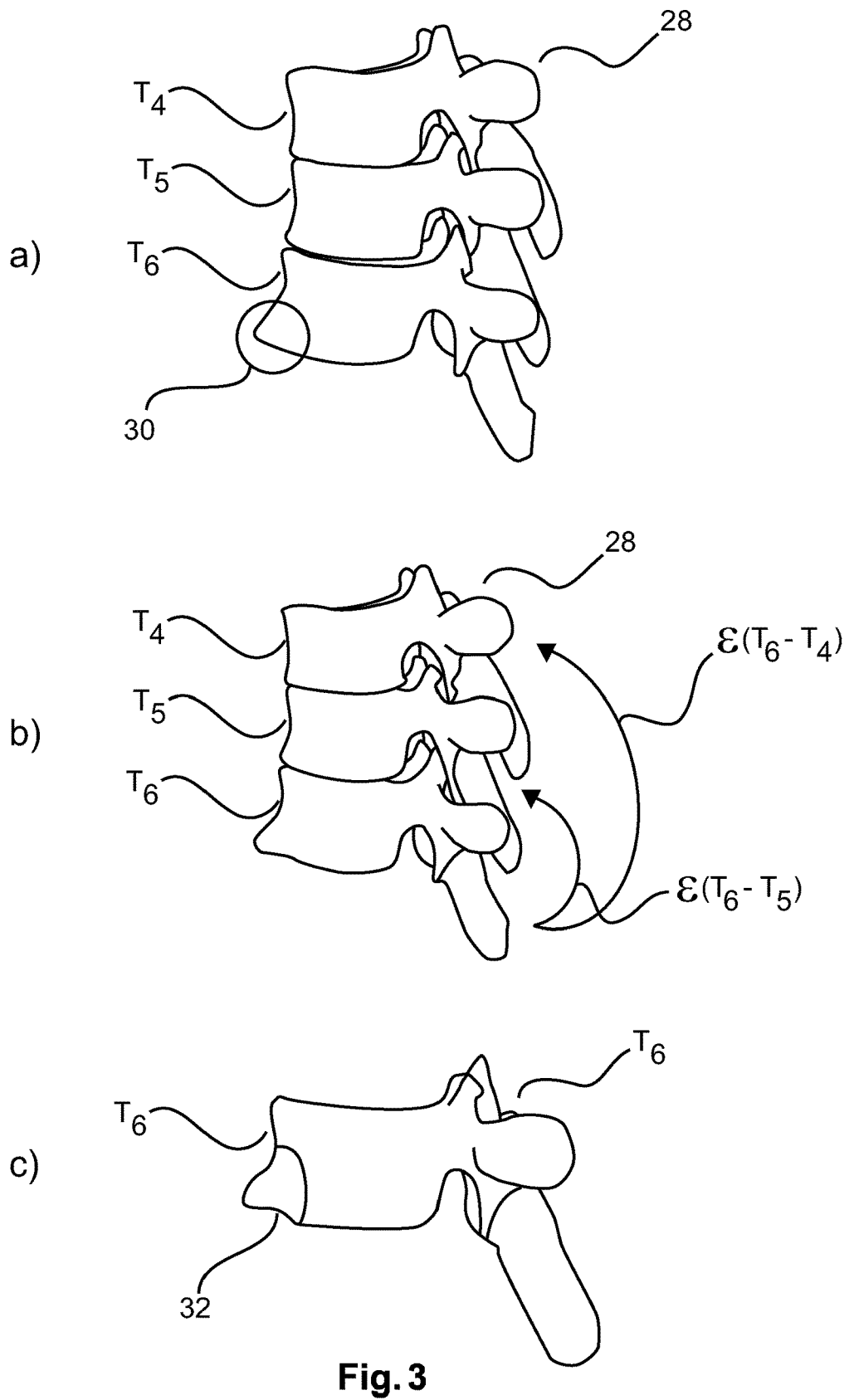
FIG. 3 shows an exemplary spinal 3D characteristic feature identification process.

FIG. 3 illustrates an approach to characterizing characteristic vertebral feature information using 3D shape comparison.

In FIG. 3A there are shown three segments of a section of a spinal column $T_4$, $T_5$, and $T_6$. This information has been acquired from processed 3D volume information, for example from a CT scanner or an MRI scanner. FIG. 3A effectively illustrates 3D spinal model data that has been derived from the processed 3D volume information by segmenting the processed 3D volume data. Shown in the section of a spinal column 28 is vertebral level $T_4$, vertebral level $T_5$ and vertebral level $T_6$. Vertebral levels $T_4$ and $T_5$ represent relatively normal vertebrae. Vertebral level $T_6$, however, has a projection 30 on its left side known as a spondylophyte. Spondylosis is an osteoarthritic degeneration of the vertebrae and the spine characterized by abnormal bony growths. Such features can be useful when characterizing individual vertebral segments.

FIG. 3B illustrates the 3D characteristic feature detection using shape registration with neighbouring vertebrae. A letter 8 denotes the function of performing the computation of shape differences.

There are various ways to identify the shape difference between two arbitrary regions of voxels.

Preferably, surface representation in 3D spinal model data is most commonly done using triangular surface meshes. Therefore, surface registration between the first and second vertebra information is performed using, for example, an iterative closest point (ICP) algorithm. After surface registration, the surface distances are calculated by finding, for each vertex on the first vertebral information, the closest point to that point on the surface of the second vertebral information. Features are then found by thresholding the distances.

According to an embodiment of the invention, an example of the method as described previously is provided, wherein in step d), the computing of the 3D characteristic vertebral feature information further comprises:
d6) performing a shape registration between the first vertebra information and the second vertebra information;
d7) computing a 3D shape difference between the registered first vertebra information and second vertebra information; and
d8) identifying a region in the first vertebra information using a computed shape difference as the 3D shape difference.

According to an embodiment, in step d6), an iterative closest point (ICP) algorithm is used to perform the shape registration.

According to an embodiment, in step d8), the region in the first vertebra information is identified by thresholding surface differences between the first vertebra information and the second vertebra information.

According to an embodiment of the invention, an example of the method as described previously is provided, wherein in step d8), the step of identifying a region in the first vertebra information comprises identifying the 3D shape difference between the registered first vertebra information and second vertebra information, which is greater than a vertebral difference threshold.

Therefore, it is possible to prevent the mis-identification of vertebral differences, which are due to natural variations in the bone surface, for example, and to only detect vertebral differences, which are significant to a medical professional.

In an alternative embodiment, the 3D vertebral shape difference between the first vertebra information and the second vertebra information is computed by superimposing upon pre-calculated centre-lines of the first and second vertebra information, and a direct subtraction of the first vertebra information, representing a first vertebral level from the second vertebra information, representing a second vertebral level, could be performed in 3D. The remaining voxels would be the 3D characteristic features.

In another alternative embodiment, a shape registration of the first vertebra information and the second vertebra information is performed. For example, a registration could be performed between $T_6$ and $T_5$, and/or $T_6$ and $T_4$. This shape registration may be extended to a larger number of vertebral segments.

As illustrated, using a technique as discussed above, or similar, a first shape difference between a first vertebral level $T_6$ and a second vertebral level $T_5$ is derived. Then, the shape difference between the first vertebral level $T_6$ and a third vertebral level $T_4$ is derived.

According to an embodiment of the invention, the derivation of the shape difference is limited to vertebrae present in a proposed 2D fluoroscopy field of view.

FIG. 3C illustrates vertebra $T_6$ with its 3D characteristic vertebral feature information 32 isolated. Because the 3D characteristic vertebral feature information is a subset of the voxels of the processed 3D volume information representing a portion of the spinal column, the 3D characteristic vertebral feature information may be viewed in different directions. In addition, the voxels constituting the 3D characteristic vertebral feature information are referenced to the geometric frame of reference of the original processed 3D volume information, enabling the production of forward projections through only the extracted the 3D characteristic vertebral feature information, or alternatively the production of forward projections of the 3D characteristic vertebral feature information, which are occluded by portions of the spinal column.

According to an embodiment of the invention, a method is provided as described previously, wherein the 3D characteristic vertebral feature information represents an anatomical feature selected from the group of: a first rib pair, a last rib pair, a sacrum, an atlas, a spondylophyte, a fracture, or an implant.

Therefore, frequently occurring spinal deformations can be used to identify 3D characteristic vertebral feature information.

Although the foregoing embodiments have discussed the acquisition of 3D characteristic vertebral feature information of a first vertebra only, it will be understood that the algorithm can be extended to compute, alone, or in combination, 3D characteristic vertebral feature information of at least a second vertebra, and/or a third vertebra, and/or a fourth vertebra, and/or a fifth vertebra, or all vertebrae present in a spinal column.

According to an embodiment of the invention, the viewing position of a 2D intra-operative fluoroscopy device along the spine of a patient is provided. Then, 3D characteristic feature information may be computed for vertebrae, which can be best seen in the viewing plane of the 2D intra-operative fluoroscopy device, at the viewing position.

The viewing position is provided as a point in the 3D frame of reference of the original processed 3D volume information. For example, the viewing position is provided as a horizontal displacement along the spine, at a certain distance from the spine, and an angular deviation from the spine.

After the identification of the 3D characteristic vertebral feature information, a series of voxel regions will be available. These voxel regions, representing characteristic features of a spinal column, will self-evidently be referenced to the geometric datum used for acquiring the processed 3D volume information. Therefore, using reconstruction techniques, an optimal patient viewing direction of the 3D vertebral features can be calculated, which optimizes the visibility of the 3D characteristic vertebral features in a 2D projection.

According to an embodiment of the invention, forward projections through the voxels representing only the 3D characteristic vertebral features are performed.

According to an embodiment of the invention, forward projections through the voxels representing the 3D characteristic vertebral features, and through the voxels representing the spinal column are performed. According to an embodiment of the invention, a method is provided as discussed previously, wherein step a) further comprises:
a1) providing target vertebral level information;
wherein step d) further comprises:
d1) determining a patient viewing direction using the 3D characteristic vertebral feature information and the target vertebral level information, wherein the patient viewing direction is determined by searching for a viewing direction, which optimizes a 3D characteristic vertebral feature visibility metric; and
wherein step e) further comprises:
e1) outputting the patient viewing direction.

According to this embodiment, the visibility of the characteristic spinal features (represented by the 3D characteristic vertebral feature information) in a 2D projection can be optimized during an intra-operative fluoroscopic image intervention.

In the previously described embodiments, the provision of target vertebral level information comprises the identification by a medical professional of a vertebral level of a patient's spinal column, which will be treated in a minimally invasive spinal intervention. For example, in FIG. 3, the level $T_5$ would be selected and input as the target vertebral level information using a computer interface, for example.

The 3D characteristic vertebral feature visibility metric provides an indication of how a certain viewing direction affects the visibility of the 3D characteristic vertebral feature information. There are many ways to calculate such a metric.

According to an embodiment of the invention, the 3D characteristic vertebral feature visibility metric is calculated by performing a plurality of forward projections through voxels representing the 3D characteristic vertebral feature information from a plurality of directions around voxel clusters.

The forward projection direction, which results in the greatest area in a 2D projection resulting from a forward projection through the 3D characteristic vertebral feature information, is the viewing direction, which optimizes a 3D characteristic vertebral feature visibility metric.

Due to the projective nature of fluoroscopy, there will be viewing directions, in which certain features can be identified more easily than others. Given a target vertebral level, characteristic features in close proximity can be selected. Using the previously described method, a viewing direction is determined such that the maximum number of these features can be identified, or that one feature is optimally viewable. In addition to shape characteristics, superimposed surrounding anatomy can also be taken into account for optimum view angle determination. After determining the characteristic feature for identification, it also need to be considered that the features are only visible in certain viewing directions.

In order to determine features that can easily be seen in a fluoroscopic projection, the range of viewing directions, for which the characteristic edges of the features are parallel are first determined. Then, simulated projection images can be calculated from the pre-operative data, such as CT data. Standard algorithms for projection are used in the step. Then, an analysis is made of the local neighbourhood around the feature, by calculating the variability of grey values within a small region of interest around the feature, or by analyzing the gradients at the feature position to detect whether or not the landmark is located on an edge. Then, features that can clearly be seen in the image can be automatically selected. The optimal view plane is then chosen such that it contains the maximum number of clearly visible features. The optimal view plane may be selected during the intervention while the range of viewing directions may be computed before or during the intervention.

According to an embodiment of the invention, in step d1) the 3D spinal model data is used to occlude the 3D characteristic vertebral feature information.

Therefore, the forward projections, which are calculated when determining the patient viewing direction, produce 2D areas in the projected view plane, which result firstly from rays projected through 3D characteristic vertebral feature information, and secondly from rays projected through 3D spinal model data. This ensures that the 3D characteristic vertebral feature visibility metric for each forward projection direction, and therefore the patient viewing direction eventually chosen, is that which enables the most characteristic features to be seen, even in the presence of the spine.

According to an embodiment of the invention, the outputting of the patient viewing direction may be in a standard format, such as a solid angle with respect to the datum of the processed 3D volume data acquired, for example, from a CT scanner.

According to an embodiment of the invention, this geometrical information is used to align equipment to provide an optimal viewing direction of the characteristic vertebral features.

Figure 4:
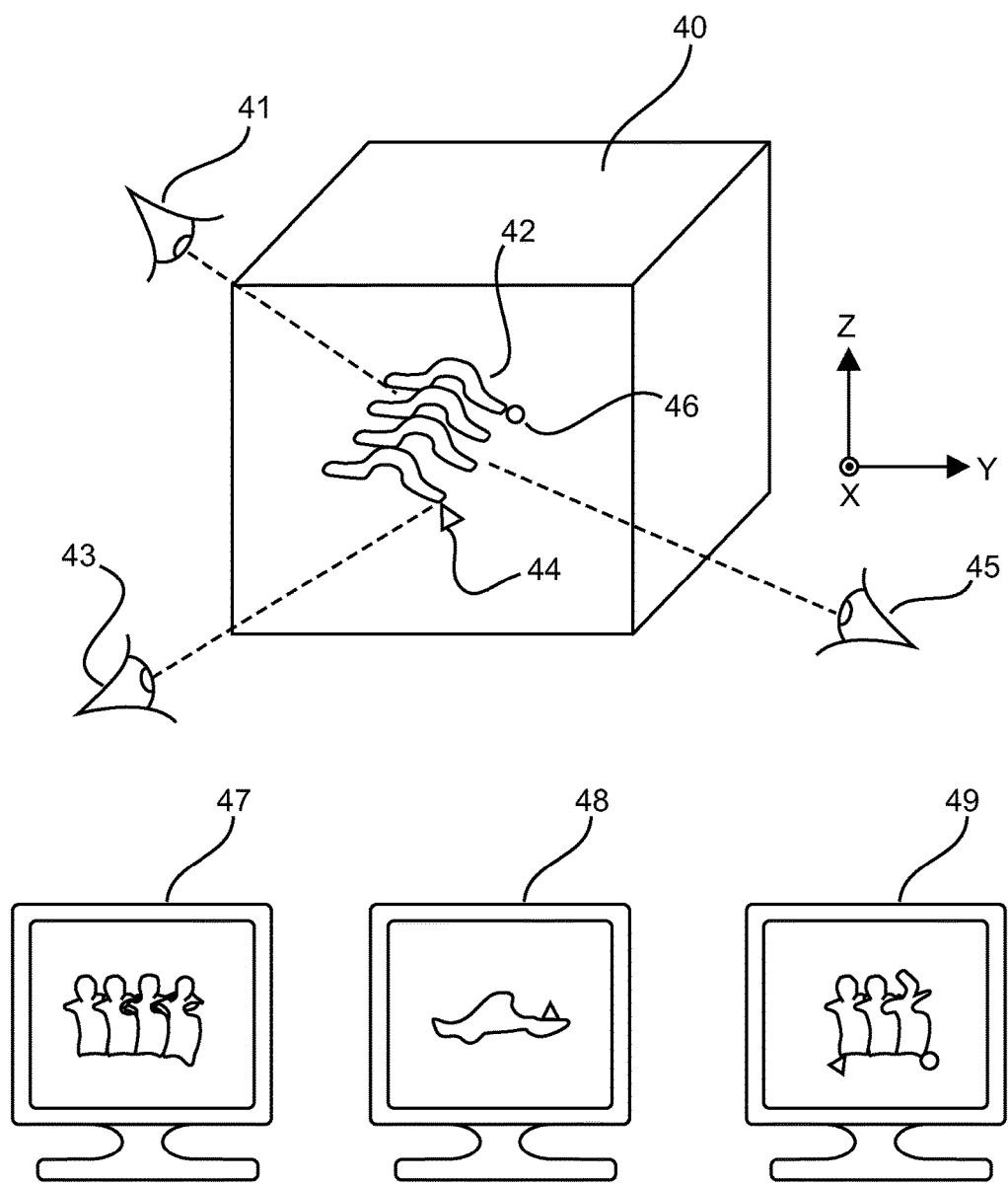
FIG. 4 shows an exemplary identification of an optimal view direction.

FIG. 4 illustrates the above-described process. A geometrical reference cube 40 containing display voxels is illustrated with a segment of spinal column inside. The spinal column has first and second characteristic features illustrated by a triangle 44, and by a circle 46. Although in this purely exemplary presentation, two characteristic vertebral features are shown on different vertebral levels, it will be understood that the algorithm would work with only one 3D characteristic vertebral feature on one vertebral level, such as only the triangle 44.

The algorithm produces forward projections at a range of different forward projection angles through a 3D spinal model data 42. The forward projection angles are illustrated from points or positions 41, 43, and 45.

An exemplary first 2D screen 47 shows the effect of a forward projection from the position 41. It can be seen that the spinal column section is viewed from the side, and the characteristic features 44 and 46 are entirely occluded by the spine itself. Therefore, this would not be a good candidate viewing direction.

An exemplary second 2D screen 48 shows a forward projection of the characteristic features from the position 43.

It can be seen that the triangular characteristic feature 44 is present, but this occludes the characteristic feature 46.

An exemplary third 2D screen 49 shows the view of the 3D characteristic vertebral feature information from the position 45. In this screen, the sides of both characteristic features 44 and 46 can be seen with ease, and this is selected as the patient viewing direction, because the 3D characteristic vertebral feature visibility metric will be optimal in this position.

Figure 5:
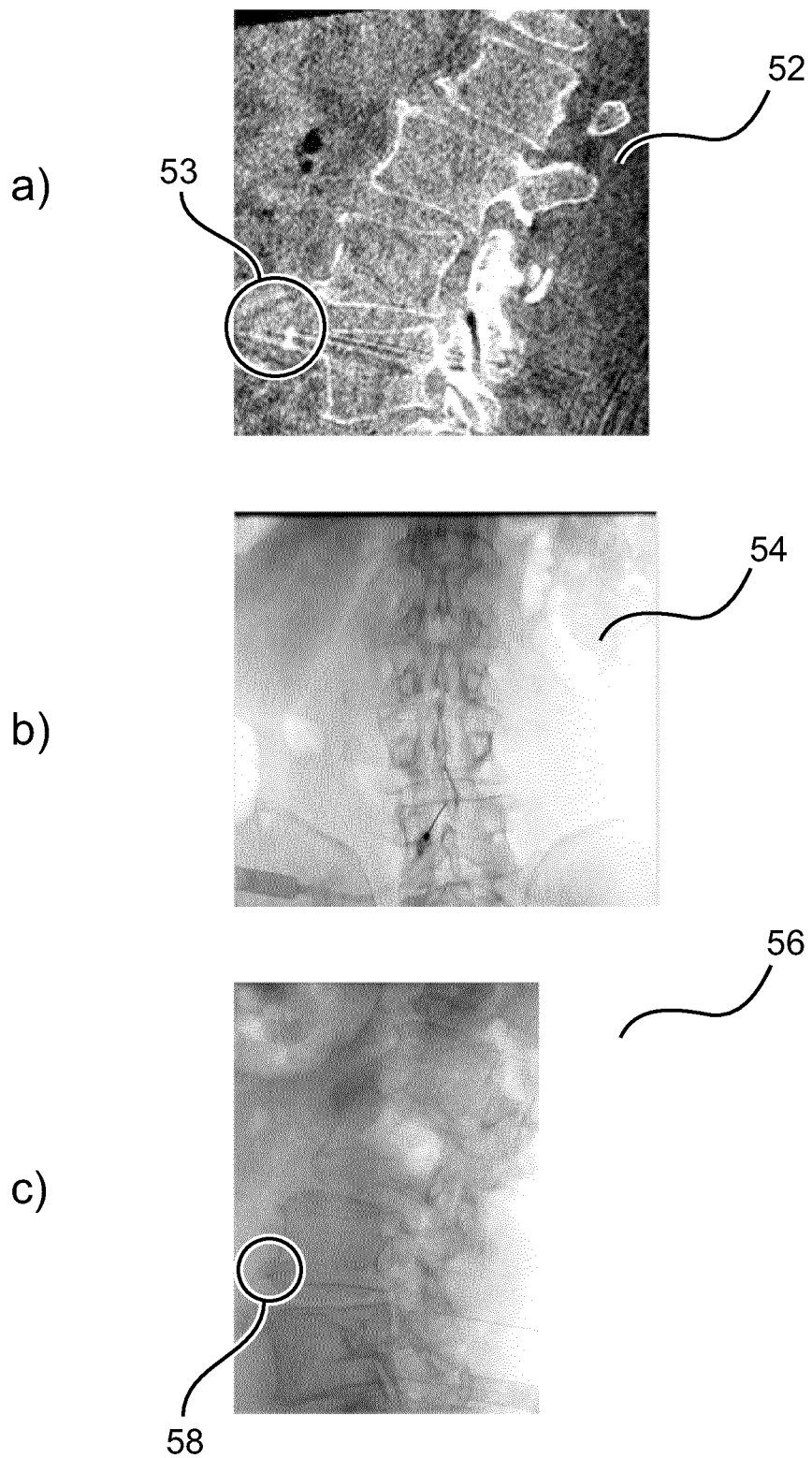
FIG. 5 shows an exemplary practical result of optimal view direction identification.
Figure 6:
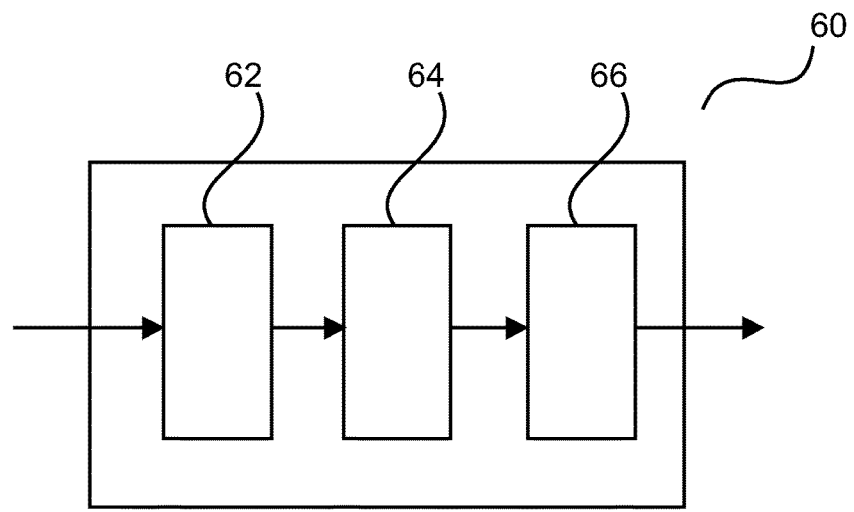
FIG. 6 shows a device for 3D characteristic vertebral feature identification according to an aspect of the invention.
Figure 7:
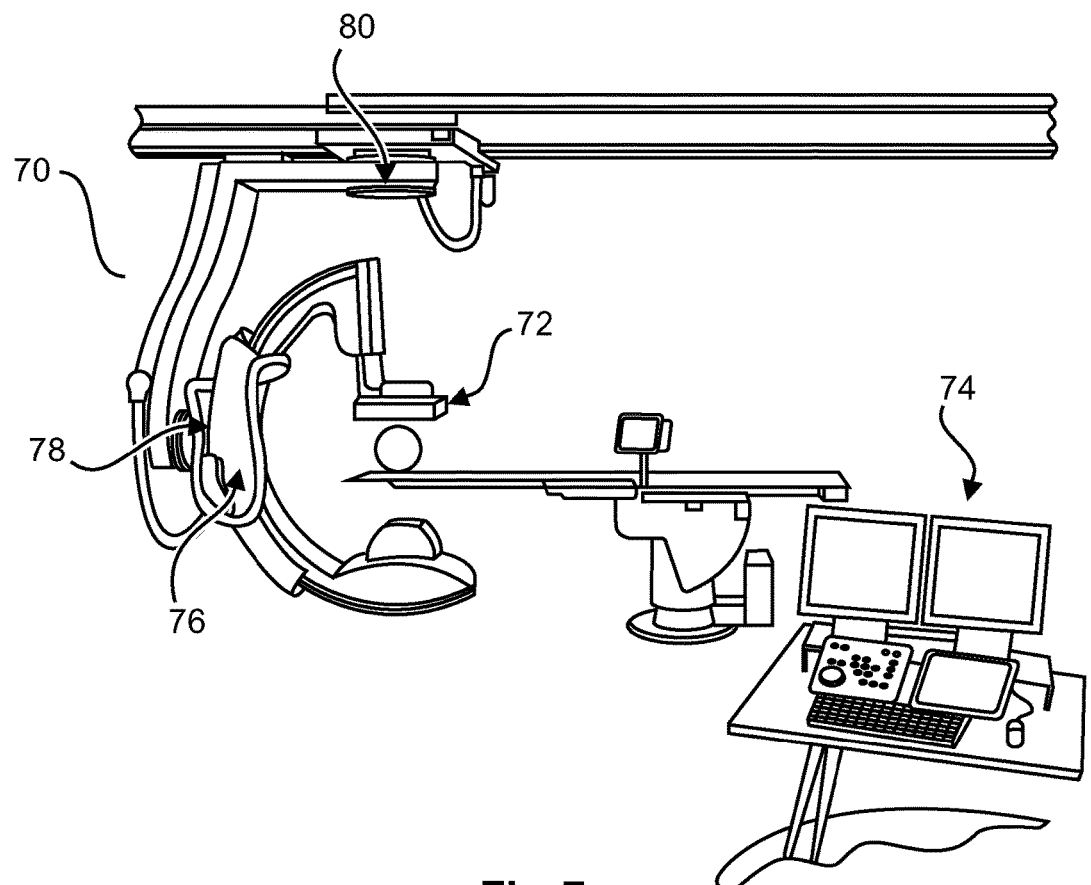
FIG. 7 shows an example of a medical imaging system according to an aspect of the invention.

FIG. 5 illustrates a clinical example where defining the correct viewing direction is important.

In FIG. 5A, a projection from processed 3D information is shown 52. A ringed area 53 shows a spondylophyte in the processed 3D information, which could be used for identification, because other vertebrae in the processed 3D information do not have such a feature.

In FIG. 5B, a fluoroscopic projection of the spinal column imaged in the processed 3D information of FIG. 5A is shown.

The fluoroscopic projection has been taken from a viewing direction (with respect to the spine), in which the spondylophyte 53 is occluded by the remainder of the spinal column. Therefore, the spondylophyte is not visible to the medical professional performing the intervention. This means that a surgical professional aiming to identify a target vertebral level of the spine using the spondylophyte from the fluoroscopic projection angle of B would have difficulty identifying the correct target vertebral level.

FIG. 5C illustrates a fluoroscopic projection 56 taken from a viewing direction, which clearly shows the spondylophyte at 58, as identified by the algorithm.

Therefore, the target vertebral level can easily be identified by a medical professional from the fluoroscopy image using the spondylophyte.

According to an embodiment of the invention, a method is provided as described previously, wherein step b) further comprises:
b1) providing 3D superimposed anatomy information from the processed 3D volume information; and
wherein step d) further comprises:
d2) calculating an occlusion metric of the 3D characteristic vertebral feature information for a plurality of synthetic viewing directions of the 3D spinal model data, wherein an occlusion is caused by an anatomical feature in the 3D superimposed anatomy information; and
d3) deriving the 3D characteristic vertebral feature visibility metric based on the occlusion metric of the 3D characteristic vertebral feature information.

Different organs inside the patient such as the liver, the heart, the lungs, and the pancreas, have different X-ray translucencies, and may affect the identification of characteristic vertebral features during a 2D fluoroscopy.

Therefore, in this embodiment, 3D superimposed anatomy information is derived from the processed 3D volume information obtained, for example from a CT scan. The occlusion of the internal organs around the spinal column is taken into account when calculating the 3D characteristic vertebral feature visibility metric. It could be the case that a patient viewing direction, which provides the optimal 3D characteristic vertebral feature visibility without taking into account the patient's anatomy might not be so optimal when taking into account the position of the liver, the lungs and other organs. It will be appreciated that the position of the patient's internal organs can easily be derived from the processed 3D volume information and used in forward projection reconstructions.

According to an embodiment of the invention, a method is provided as discussed previously, wherein step i) further comprises:
e2) aligning a patient imaging system based on the determined patient viewing direction.

Patient imaging systems are provided on electrically-positionable frames, with electro-mechanical drives, which can be interfaced to a control system, such as a computer control system. Provided a geographical datum of the processed 3D volume information, the patient imaging system, and the current alignment of a patient are accounted for, it is possible for a patient imaging system to be aligned with respect to a patient, using the determined patient viewing direction.

Therefore, a patient imaging system may be automatically aligned to provide the optimal imaging direction based on 3D volume data representing a portion of a spinal column, providing a more convenient and accurate self-alignable item of medical imaging equipment.

According to an embodiment of the invention, the patient imaging system is an electro-mechanically alignable fluoroscopy system.

The optimum viewing angle (related to the optimal view plane) is communicated to the user (or directly to the imaging system). Fluoroscopy projections are made using that viewing angle. The pre-interventional data is displayed to the user as volumetric, or as a slice display, or as a simulated projection, with the identified characteristic landmarks and the target vertebral level indicated.

According to an embodiment of the invention, a method is provided as discussed previously, wherein step a) further comprises:
a2) providing processed 2D live intervention data, representing a portion of a spinal column during a surgical intervention;
wherein step d) further comprises:
d4) registering the 2D live intervention image data to the 3D characteristic vertebral feature data; and
d5) providing a 2D augmented intervention image by projecting the 3D characteristic vertebral feature data onto the 2D live intervention image from the patient viewing direction; and
wherein step e) further comprises:
e3) displaying the augmented intervention image.

Therefore, the live 2D fluoroscopy data is augmented with a forward projection of the 3D characteristic vertebral feature data at the same angle as the patient viewing direction used with the fluoroscopy equipment during the intervention.

Because the 2D live intervention image data will be aligned in the same viewing plane as the forward projection of the 3D characteristic vertebral feature data; it is possible to highlight, or to "ghost" the characteristic vertebral feature data into the 2D live intervention image data view. This ensures that during a minimally invasive intervention, the target vertebral level is correctly identified.

The augmented live intervention image provides enhanced feedback about the location of characteristic features on the spine. Therefore, the user can identify the 3D characteristic features during a live fluoroscopy, and then as a reference determines the appropriate target vertebral level for treatment.

According to an embodiment of the invention, a device 60 for 3D characteristic vertebral feature identification is provided. The device comprises an input unit 62, a processing unit 64, and an output unit 66

The input unit 62 is configured to provide processed 3D volume information representing a portion of a spinal column, wherein the processed 3D volume information is computed from a plurality of images obtained through the spinal column, and is acquired along a plurality of acquisition directions.

The processing unit 64 is configured to generate 3D spinal model data derived from the processed 3D volume information, to select first vertebra information and second vertebra information in the 3D spinal model data, to compute 3D characteristic vertebral feature information of the first vertebra by computing a 3D vertebra shape difference between the first vertebra information and the second vertebra information in the 3D spinal model data.

The output unit 66 is configured to output the 3D characteristic vertebral feature information.

The device 60 may be implemented as a software programme executing on a computer processor, with input and output interface circuitry. Alternatively, processing may be performed by a digital signal processor, an FPGA, an ASIC, or combinations of these.

According to an embodiment of the invention, an example of the device 60 is provided as discussed previously, wherein the input unit 62 is further configured to provide target vertebral level information. The processing unit 64 is further configured to determine a patient viewing direction using the 3D characteristic vertebral feature information and the target vertebral level information, wherein the patient viewing direction is determined by searching for a viewing direction, which optimizes a 3D characteristic vertebral feature visibility metric. The output unit 66 is further configured to output the patient viewing direction.

According to an embodiment of the invention, an example of the device 60 is provided according to the previous description, wherein the processing unit 64 is further configured to generate 3D superimposed anatomy information from the processed 3D volume information, to calculate an occlusion metric of the 3D vertebral shape difference for a plurality of synthetic viewing directions of the 3D spinal model data, wherein an occlusion is caused by an anatomical feature in the 3D superimposed anatomy information, and to derive the 3D characteristic vertebral feature visibility metric based on the occlusion metric of the 3D characteristic vertebral feature information.

According to an embodiment of the invention, an example of the device 60 is provided according to the previous description, wherein the output unit 66 is further configured to align a medical imaging acquisition arrangement based on the determined patient viewing direction.

According to an embodiment of the invention, an example of the device 60 is provided according to the previous description, wherein the input unit 62 is further configured to provide processed 2D live intervention image data, representing a portion of a spinal column during a surgical intervention. The processing unit 64 is further configured to register the 2D live intervention image data to the 3D characteristic vertebral feature data, to provide a 2D augmented intervention image by projecting the 3D characteristic vertebral feature data onto the 2D live intervention image data from the patient viewing direction. The output unit 66 is further configured to display the augmented intervention image.

According to an embodiment of the invention, an example of the device 60 is provided as described previously, wherein the processing unit 64 is further configured to segment the processed 3D volume information to provide 3D spinal model data from the processed 3D volume information.

According to an embodiment of the invention, an example of the device 60 is provided as described previously, wherein the processing unit 64 is further configured to compute the 3D characteristic vertebral feature information by performing a shape registration between the first vertebra information and the second vertebra information, by computing a shape difference between the registered first vertebra information and second vertebra information, and by identifying a region in the first vertebra information using the computed shape difference as the 3D shape difference.

According to an embodiment of the invention, an example of the device 60 is provided according to the previous description, wherein the processing unit 64 is configured to identify the 3D vertebral shape difference between the registered first vertebra information and second vertebra information, which is greater than a vertebral difference threshold.

According to an aspect of the invention, a medical imaging system 70 is provided. The medical imaging system 70 comprises a medical imaging acquisition arrangement 72 and an image processing arrangement 74.

The image processing arrangement 72 is provided as a device as previously described.

According to an embodiment of this aspect, the medical imaging system 70 is provided as described previously, wherein the medical imaging acquisition arrangement 72 further comprises an imager alignment mechanism 76. The image processing arrangement 74 is provided as a device according to the previous description, and the imager alignment mechanism 76 is configured to be aligned based on the patient viewing direction output from the image processing arrangement 74. The imager alignment mechanism comprises electro-mechanical drives controlling an azimuth 80 and an elevation 78 of the fluoroscopic imager 72.

According to this aspect of the invention, it is possible to align automatically a medical imaging system, which for example may include a 2D fluoroscopy imager, according to characteristic features on input 3D volume data acquired from a pre-operative CT scan.

According to an embodiment of the invention, a medical professional may select certain characteristic features in the 3D volume data, and the medical imaging acquisition arrangement may be aligned, based only on the optimal viewing direction for the selected features.

Therefore, when performing a minimally invasive spinal intervention, it is possible to arrange a medical imaging acquisition arrangement at an optimal angle, in a convenient manner, to ensure that mis-identification of target vertebral levels does not occur.

According to an embodiment of the invention, the image processing arrangement 74 further comprises a pre-operative processing application, executed on a computer. A user may use an interface of the a pre-operative processing application to position a "field of view" frame in a user interface of the application, corresponding to the field of view of the fluoroscopy equipment, over a displayed relevant section of spinal column, to pre-compute the 3D characteristic features.

According to an embodiment of the invention, the image processing arrangement 74 further comprises alignment monitoring means connected to the image processing arrangement 74. The alignment monitoring means is configured to monitor a change in the alignment of the medical imaging acquisition arrangement 72. When a change in the alignment of the medical imaging acquisition arrangement 72, relative to the patient, is detected, the image processing arrangement 74 recomputes the 3D characteristic vertebral feature information.

Therefore, if the a medical imaging acquisition arrangement 72 is translated horizontally along the patient, or around the patient, image processing arrangement 74 can display an updated enhanced 2D fluoroscopy view, showing the expected 3D vertebral characteristic features, which will be visible in the changed field of view.

According to an aspect of the invention, a computer program element for controlling a device for displaying medical images acquired from a target is provided according to the previous description. The computer program element, when being executed by a processing unit, is adapted to perform the method steps as discussed above.

According to an aspect of the invention, a computer-readable medium having stored the program as described above is provided.

A computer program element might therefore be stored on a computer unit, which might also be part of an embodiment of the present invention. This computing unit may be adapted to perform or induce performance of the steps of the method described above.

Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both the computer program that has the invention installed from the beginning, and a computer program that by means of an update turns an existing program into a program that uses the invention.

A computer program may be stored and/or distributed on a suitable medium, such as optical storage media or a solid state medium supplied together with, or as a part of other hardware, but may also be distributed in other forms, such as via the Internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It should to be noted that embodiments of the invention are described with reference to different subject-matters. In particular, some embodiments are described with reference to method-type claims, whereas other embodiments are described with reference to the device-type claims. However, a person skilled in the art will gather from the above, and the following description that, unless otherwise notified, in addition to any combination of features belonging to one type of subject-matter, also any other combination between features relating to different subject-matters is considered to be disclosed with this application.

All features can be combined to provide a synergetic effect that is more than the simple summation of the features.

While the invention has been illustrated and described in detail in the drawings and foregoing description, such illustration and description are to be considered illustrative or exemplary, and not restrictive. The invention is not limited to the disclosed embodiments.

Other variations to the disclosed embodiments can be understood, and effected by those skilled in the art in practicing the claimed invention, from a study of the drawings, the disclosure, and the dependent claims.

In the claims, the word "comprising" does not exclude other elements or steps, and the indefinite article "a" or "an" does not exclude a plurality. A single processor, or other unit, may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A device for 3D characteristic vertebral feature identification comprising:
an input unit;
a processing unit; and
an output unit;
wherein the input unit is configured to provide processed 3D volume information representing a portion of a spinal column, wherein the processed 3D volume information is computed from a plurality of images obtained through the spinal column, and is acquired along a plurality of acquisition directions;
wherein the processing unit is configured to generate 3D spinal model data derived from the processed 3D volume information, to select first vertebra information and second vertebra information in the 3D spinal model data; and to compute 3D characteristic vertebral feature information of the first vertebra by computing a 3D vertebral shape difference between the first vertebra information and the second vertebra information in the 3D spinal model data;
wherein the input unit is further configured to provide target vertebral level information;
wherein the processing unit is further configured to determine a patient viewing direction using the 3D characteristic vertebral feature information and the target vertebral level information,
wherein the patient viewing direction is determined by searching for a viewing direction, which optimizes a 3D characteristic vertebral feature visibility metric; and
wherein the output unit is further configured to output the patient viewing direction.

2. The device according to claim 1,
wherein the processing unit is further configured to generate 3D superimposed anatomy information from the processed 3D volume information, to calculate an occlusion metric of the 3D vertebral shape difference for a plurality of synthetic viewing directions of the 3D spinal model data, wherein the occlusion is caused by an anatomical feature in the 3D superimposed anatomy information, and to derive the 3D characteristic vertebral feature visibility metric based on the occlusion metric of the 3D characteristic vertebral feature information.

3. The device according to claim 1,
wherein the output unit is further configured to align a medical imaging acquisition arrangement based on the determined patient viewing direction.

4. The device according to claim 1,
wherein the input unit is further configured to provide processed 2D live intervention image data, representing a portion of a spinal column during a surgical intervention;

wherein the processing unit is further configured to register the 2D live intervention image data to the 3D characteristic vertebral feature information, and to provide a 2D augmented intervention image by projecting the 3D characteristic vertebral feature data information onto the 2D live intervention image data from the patient viewing direction; and wherein the output unit is further configured to display the augmented intervention image.

5. The device according to claim 1,
wherein the processing unit is further configured to segment the 3D volume information to provide 3D spinal model data from the 3D volume information.

6. The device according to claim 5,
wherein the processing unit is further configured to compute the 3D characteristic vertebral feature information by performing a shape registration between the first vertebra information and the second vertebra information, by computing a shape difference between the registered first vertebra information and second vertebra information, and by identifying a region in the first vertebra information using the computed shape difference as the 3D vertebral shape difference.

7. The device according to claim 6,
wherein the processing unit is configured to identify the 3D vertebral shape difference between the registered first vertebra information and second vertebra information, which is greater than a vertebral difference threshold.

8. A medical imaging system, comprising:
a medical imaging acquisition arrangement; and
an image processing arrangement;
wherein the image processing arrangement is provided as a device according to claim 7.

9. The medical imaging system of claim 8,
wherein the medical imaging acquisition arrangement further comprises an imager alignment mechanism;
wherein the image processing arrangement is provided as a device; and
wherein the imager alignment mechanism is configured to be aligned based on the patient viewing direction output from the image processing arrangement.

10. A method for 3D characteristic vertebral feature identification using processed 3D volume information, comprising acts of:
providing the processed 3D volume information representing a portion of a spinal column, wherein the processed 3D volume information is computed from a plurality of images obtained through the spinal column, and is acquired along a plurality of acquisition directions;
generating 3D spinal model data derived from the processed 3D volume information;
selecting first vertebra information and second vertebra information in the 3D spinal model data;
computing 3D characteristic vertebral feature information of the first vertebra by computing a 3D vertebral shape difference between the first vertebra information and the second vertebra information in the 3D spinal model data;
  wherein the providing act includes an act of providing target vertebral level information;
  wherein the computing act includes an act of determining a patient viewing direction using the 3D characteristic vertebral feature information and the target vertebral level information, wherein the patient viewing direction is determined by searching for a viewing direction, which optimizes a 3D characteristic vertebral feature visibility metric; and
outputting the patient viewing direction.

11. The method according to claim 10,
wherein the outputting act includes an act of aligning a patient imaging system based on the determined patient viewing direction.

12. A non-transitory computer readable medium comprising computer instructions which, when executed by a processor, configure the processor to perform a method for 3D characteristic vertebral feature identification using processed 3D volume information, the method comprising acts of:
providing the processed 3D volume information representing a portion of a spinal column, wherein the processed 3D volume information is computed from a plurality of images obtained through the spinal column, and is acquired along a plurality of acquisition directions;
generating 3D spinal model data derived from the processed 3D volume information;
selecting first vertebra information and second vertebra information in the 3D spinal model data;
computing 3D characteristic vertebral feature information of the first vertebra by computing a 3D vertebral shape difference between the first vertebra information and the second vertebra information in the 3D spinal model data;
wherein the providing act includes an act of providing target vertebral level information;
wherein the computing act includes an act of determining a patient viewing direction using the 3D characteristic vertebral feature information and the target vertebral level information, wherein the patient viewing direction is determined by searching for a viewing direction, which optimizes a 3D characteristic vertebral feature visibility metric; and
outputting the patient viewing direction.

* * * * *